United States Patent [19]

Sehm

[11] Patent Number: 5,221,722

[45] Date of Patent: Jun. 22, 1993

[54] CROSSLINKED POLYACRYLIC ACID

[75] Inventor: Eugene J. Sehm, Akron, Ohio

[73] Assignee: The B. F. Goodrich Company, Akron, Ohio

[21] Appl. No.: 965,091

[22] Filed: Oct. 22, 1992

Related U.S. Application Data

[63] Continuation-in-part of Ser. No. 782,754, Oct. 21, 1991, abandoned, which is a continuation of Ser. No. 466,555, Jan. 17, 1990, abandoned, which is a continuation of Ser. No. 276,839, Nov. 28, 1988, abandoned.

[51] Int. Cl.$^5$ .............................................. C08F 2/00
[52] U.S. Cl. .............................. 526/230.5; 526/318.5; 526/930; 526/936; 523/111
[58] Field of Search ................... 526/230.5, 318.5, 930, 526/936; 523/111

[56] References Cited

U.S. PATENT DOCUMENTS

| | | | |
|---|---|---|---|
| 3,297,664 | 1/1967 | Miskel et al. | 523/111 |
| 4,758,641 | 7/1988 | Hsu | 526/208 |

*Primary Examiner*—Joseph L. Schofer
*Assistant Examiner*—Jeffrey T. Smith
*Attorney, Agent, or Firm*—George W. Moxon, II

[57] ABSTRACT

Polycarbophil or crosslinked acrylic acid polymer is prepared in a solvent selected from acetone, alkyl acetates, and mixtures thereof, in the presence of an effective amount of divinyl glycol crosslinker, and in the presence of an effective amount of a suitable initiator allowing for polymerization to proceed at a temperature below 100° C. at atmospheric pressure. The polymer produced has average particle size of less than 10 microns without grinding, its viscosity is greater than about 20,000 cPs when measured in water at 1% concentration, and it adheres to mucous membranes. By preparing the polymer in a non-aqueous solvent, the need for aqueous washing is avoided and the subsequent and enormous swelling of the polymer is avoided which means that prolonged and excessive drying inherent in the known processes is avoided.

10 Claims, No Drawings

CROSSLINKED POLYACRYLIC ACID

This is a continuation-in-part of application Ser. No. 07/782,754 filed Oct. 21, 1991, now abandoned, which is a file wrapper continuation of Ser. No. 07/466,555 filed Jan. 17, 1990, now abandoned, which is in turn a continuation of Ser. No. 07/276,839 filed Nov. 28, 1988, now abandoned.

BACKGROUND OF THE INVENTION

Polymers of unsaturated carboxylic acids and salts thereof are well known. These polymers include homopolymers and copolymers which contain up to 10 weight percent of other copolymerizable monomers. Typical monomers include acrylic acid, methacrylic acid, maleic acid or its anhydride, itaconic acid, and the like. U.S. Pat. No. 2,798,053, for instance, discloses copolymers of acrylic acid with small amounts of polyalkenyl polyether crosslinkers which are gel-like and, especially in the form of their salts, can absorb large quantities of water or solvents with subsequent substantial increase in volume. U.S. Pat. Nos. 3,940,351 and 4,062,817 describe polymers of an unsaturated carboxylic acid and at least one acrylic or methacrylic ester wherein the alkyl groups contain 1 to 30 carbon atoms. Such polymers are also effective thickening agents, even in the presence of substantial amounts of inorganic salts. U.S. Pat. Nos. 3,915,921 and 4,066,583 disclose preparation of same or similar polymers in similar systems.

U.S. Pat. No. 4,267,103 discloses polymers of unsaturated carboxylic acids or salts thereof in certain solvents wherein more than 1% by weight of the carboxyl groups are neutralized. Such polymers have molecular weight greater than 500 and up to several million, but generally, in the range of 10,000 to one million. Such polymers are also effective thickening agents.

U.S. Pat. No. 4,758,641 discloses polymerization of acrylic acid in a solvent selected from acetone, alkyl acetates, and mixtures thereof. Polymerization is carried out in the presence of an effective amount of an initiator and crosslinker and some of the carboxyl groups on the acrylic acid are neutralized.

Polycarbophil is defined as polyacrylic acid crosslinked with divinyl glycol. Polycarbophil, therefore, is a free acid polymer which has numerous applications due to its capacity to absorb fluids, such as water, and its bioadhesive property of being able to adhere to a mucous membrane in the eyes, nose, mouth, gastrointestinal tract, vaginal cavity and rectal canal. A salt of Polycarbophil, such as calcium Polycarbophil, does not have the bioadhesive property and is not used in applications where the material would be expected to attach itself.

In the past, Polycarbophil was made by polymerizing acrylic acid monomer in a concentrated aqueous salt solution, such as magnesium sulfate, or another water soluble nonredox multivalent inorganic salt, in the presence of an initiator and the divinyl glycol crosslinker. The resulting polymer was washed with water several times whereupon it swelled to many times its volume, to remove the salt therefrom. After washing with water, the swollen polymer was dried until a solid chunk of the polymer was obtained, which was only a fraction of its swollen size. The dried polymer was then ground to the desired particle size and used in applications where its swelling property and/or its bioadhesive property were needed.

To reduce the drying cost, the polymer, after its formation, was treated with calcium carbonate or calcium hydroxide whereby the swollen polymer was collapsed upon formation of the calcium Polycarbophil. The calcium Polycarbophil was dried to a solid chunk and then ground to the desired particle size. Whereas Polycarbophil has swelling and bioadhesive properties that make it difficult to pass through the wet mouth, calcium Polycarbophil is ideally suited for oral dose form as it does not swell or become slimey in the mouth. The free acid polymer is liberated in the acid stomach from the calcium Polycarbophil.

Due to the extended and costly manufacturing procedure, only the salt of Polycarbophil is generally available.

SUMMARY OF THE INVENTION

Acrylic acid monomer is polymerized in a non-aqueous solvent selected from acetone and alkyl acetate of 1 to 6 carbon atoms in the alkyl group and in the presence of an initiator and divinyl glycol crosslinker whereby the polymer is obtained in particulate form of less than 10 microns average particle size without grinding which gives mucilage viscosity in excess of 20,000 centipoise (cPs), and sometimes in excess of 50,000 cPs when measured in 1% concentration in water. This preparation process avoids the expensive drying and grinding and retains the swelling, small particle size and bioadhesivity attributes of Polycarbophil.

DETAILED DESCRIPTION OF THE INVENTION

This invention pertains to Polycarbophil and salts thereof and to preparation thereof in a solvent selected from acetone and alkyl acetates containing 1 to 6 carbon atoms in the alkyl group in the presence of a suitable initiator and divinyl glycol (3,4-dihydroxy-1,5-hexadiene) crosslinker. Polycarbophil and alkali metal and alkaline earth metal salts thereof, prepared in this manner, have the attributes of bioadhesivity, small particle size without grinding and viscosity of above 20,000 cPs when 1% by weight mucilages thereof are measured in water. It is estimated that weight average molecular weight of Polycarbophil or crosslinked polyacrylic acid is in the range of 100,000 to 10 million, preferably one half million to 5 million.

The polyacrylic acid of this invention is a water-insoluble, crosslinked carboxy-functional polymer that contains specified amounts of carboxyl functionality and crosslinking agent. In addition, the polymer of this invention is also a useful bioadhesive which exhibits adhesion between two pieces of freshly excised rabbit stomach tissue of at least 50 dynes/cm$^2$ when measured in the manner described in U.S. Pat. No. 4,615,697.

As already pointed out, Polycarbophil is described as being polyacrylic acid crosslinked with divinyl glycol. Suitable monomer herein, therefore, is acrylic acid and salts thereof.

To prevent gelling of the polymer and to promote discrete particle formation during polymerization, at least a part of the carboxyl groups should be neutralized with a group I-A metal compound in the form of a hydroxide, oxide, or carbonate, and the like. Examples of these include sodium, potassium, and the like, as well as reaction with ammonia and certain amines including morpholine, mono, di and triethanolamine, mono propanolamine, and other amines where the partial polymeric salt is less soluble in the reaction medium.

Preferably greater than 0.1% by weight of the carboxyl groups on the monomer are neutralized or formed into a salt of the above listed materials. More preferably, greater than 1% by weight and up to about 10% by weight of the carboxyl groups are neutralized or converted to the equivalent salt prior to polymerization, especially less than about 5%. Normally, polar and medium to strongly hydrogen bonded solvents are not suitable as solvents for carboxyl containing polymers free of the salts because they swell the free acid containing polymers to gels, which is undesirable.

Solvents suitable herein are those which are liquid at room temperature of about 22° C. selected from acetone and lower alkyl acetates containing 1 to 6, preferably 2 to 4, carbon atoms in the alkyl group. Specific examples of such acetates include ethyl acetate, isopropyl acetate, n-butyl acetate, and the like. Preferred solvent is ethyl acetate. Amount of the solvent used should be such that the monomer solids content is up to about 30% by weight, preferably 10 to 20%. With the solvents enumerated herein, there is no need for washing with water to remove magnesium sulfate, or another salt which is soluble in water. The solvents suitable herein are removed by evaporation or by drying. In this way, water-washings are avoided and the problems associated with swelling of the acrylic acid polymer when contacted with water is also absent since in solvents described herein, the product does not swell nearly as much.

It was unexpectedly discovered that polyacrylic acid partially crosslinked with divinyl glycol prepared in different solvents in the manner described herein did not yield 1% mucilages with viscosity exceeding 20,000 cPs at pH 7.2-7.8 at 20 rpm having particle size less than 10 microns. Results of these experiments are given below in Table I:

TABLE I

| Polymerization Medium | Average Particle Size | Brookfield Viscosity, cPs |
|---|---|---|
| Ethyl Acetate | <10μ | 59,200 |
| Methylene Chloride | <10μ | 1,000 |
| Benzene | <10μ | 1,730 |
| 35% MgSO$_4$ | <12μ | 628 |

The polyacrylic acid made in 35% aqueous solution of magnesium sulfate was ground to the average particle size of less than about 12 microns. The other acrylic acid polymers all had average particle size of less than about 10 microns as prepared without grinding.

As is apparent from Table I, above, only polymerization of acrylic acid in ethyl acetate yielded a polymer which, in the form of a 1% mucilage, gave viscosity in excess of 20,000 cPs, and in fact was in excess of 50,000 cPs.

Amount of water in the solvent should be as low as possible since if water is allowed to exceed about 3% in the solvent, the reaction mass becomes a solid, rubbery mass, which is undesirable. Desirable results can be achieved by continuously removing water from the solvent as by passing the solvent through a distillation column or through a bed of a desiccant or a substance which will remove water from the solvent. This problem is compounded by the fact that the polymerization produces water as a by-product. However, water can be removed and amount thereof in the reaction mass can be controlled to a level below 3%, preferably 0.05 to 1%, in the solvent, in the manner described above.

Polymerization of the acrylic acid monomer or its salt in the solvent medium is usually carried out in the presence of a free radical initiator in a closed vessel in an inert atmosphere and under autogenous pressure, artificially-induced pressure, or in an open vessel under reflux at atmospheric pressure. Temperature of the polymerization may be varied up to about 100° C., preferably about 40° to 80° C., depending on the type of initiator selected. Suitable free radical initiators are those which will convert essentially all of the monomer to polymer at the reaction temperature. Examples of such free radical initiators include di(2-ethylhexyl) peroxydicarbonate, di(sec-butyl) peroxydicarbonate, di(isopropyl) peroxydicarbonate, dicyclohexyl peroxydicarbonate, dicetyl peroxydicarbonate, di(n-propyl) peroxydicarbonate, lauroyl peroxide, and other like peroxides and peroxydicarbonates. The di(2-ethylhexyl) peroxydicarbonate is effective at a reaction temperature of 45° to 55° C. whereas lauroyl peroxide is effective at a reaction temperature of 70° to 80° C. Amount of the initiator is generally less than 5%, preferably 0.05 to 2.0%, and especially 0.1 to 1% by weight based on the weight of the monomer charge.

The crosslinker for making Polycarbophil is divinyl glycol or 3,4-dihydroxy-1,5-hexadiene. Amount of the crosslinker per 100 weight parts monomer can vary up to about 5% by weight, preferably 0.01 to 3%, especially 0.5 to 2% by weight.

It was not apparent, based on the known prior art, that preparation of acrylic acid homopolymer in ethyl acetate with divinyl glycol crosslinker would result in a polymer which would have sufficient viscosity in water. This conclusion is based on the fact that the prior art did not provide any guidance as to what could be expected in terms of obtaining viscosity in excess of about 50,000 cPs with divinyl glycol crosslinker in a specific solvent. The following Table II summarizes results of polymerization of acrylic acid in an identical manner in different solvents and with different crosslinkers, wherein "NO" indicates that viscosity in excess of about 20,000 cPs was not attained when measured as a 1% concentration of the polymer in water and "YES" indicates that such viscosity was attained:

TABLE II

| Crosslinker | Solvent | | | | |
|---|---|---|---|---|---|
| | MgSO$_4$/H$_2$O | CH$_2$Cl$_2$ | C$_6$H$_6$ | EtAc/CH | EtAc |
| Allyl Sucrose (AS) | NO | YES | YES | YES | YES |
| Allyl Pentaeritol (APE) | NO | YES | YES | YES | YES |
| Divinyl Glycol (DVG) | YES | NO | NO | NO | YES |

The MgSO$_4$/H$_2$O solvent was a saturated aqueous solution of magnesium sulfate or about 35% by weight of magnesium sulfate salt in water; the CH$_2$Cl$_2$ solvent was methylene chloride; the C$_6$H$_6$ solvent was benzene; the EtAc/CH solvent was an azeotrope mixture of ethyl acetate and cyclohexane or about 54/46 ethyl acetate to cyclohexane on weight bases; and the EtAc solvent was ethyl acetate.

On the basis of the data in Table II, above, it was not possible for a person skilled in this art to predict what the expectation might be with respect to viscosity of polyacrylic acid prepared with divinyl glycol crosslinker. Preponderance of the evidence indicates that with divinyl glycol crosslinker in ethyl acetate, viscosity would be below about 20,000 cPs when measured at 1% concentration of the polymer in water. A contrary result, however, was obtained.

Preparation of calcium Polycarbophil or another salt of Polycarbophil can be made after Polycarbophil is made. This can be accomplished by treating Polycarbophil with a material such as calcium carbonate or calcium hydroxide to convert Polycarbophil to a salt thereof, such as calcium Polycarbophil.

The products of this invention have exceptional bioadhesive properties. The small particle size of the products herein lends itself to better adhesion to mucous membranes and to more extensive applications in non-tablet areas such as lotions, suspensions, gels, syrups and the like. Mix smoothness is exceptionally good and useful in drug and cosmetic applications.

The invention will now be illustrated with examples of preparing Polycarbophil or polyacrylic acid crosslinked with a small amount of divinyl glycol. The polyacrylic acid product has bioadhesive property and a particle size of less than 10 microns without grinding and its 1% aqueous solution viscosity can exceed 20,000 cPs.

EXAMPLE

A 39-gallon pilot-plant, jacketed reactor was used in this preparation which reactor had cooling capability. The following ingredients were used in amounts indicated to prepare the Polycarbophil:

| | |
|---|---|
| Ethyl Acetate Solvent | 76.21 kilograms |
| Acrylic Acid Monomer | 10.89 kilograms |
| Potassium Carbonate | 156.74 grams |
| Divinyl Glycol (DVG) Crosslinkers | 217.7 grams |
| EHP (di(2-ethylhexyl) peroxydicarbonate) Initiator | 27.22 grams |

The reactor was purged with nitrogen to remove moisture and to maintain an inert atmosphere in the reactor. The acrylic acid was preneutralized with anhydrous potassium carbonate by mixing potassium carbonate in acrylic acid until potassium carbonate dissolved in acrylic acid, which took about one-quarter of an hour, while the nitrogen purge was continued. The ethyl acetate was charged to the purged reactor followed by neutralized acrylic acid. The crosslinker was prepared in ethyl acetate and then charged to the reactor. The solution in the reactor was agitated for a few minutes and then agitation was stopped and the nitrogen purge was placed at bottom of reactor and the contents of the reactor were purged with nitrogen for about 20 minutes. With the nitrogen purge at top of reactor again, the initiator was charged to reactor and heating of the reactor was commenced and was continued for 6 hours.

The polymer recovered from the reactor was rotary vacuum dried to remove remaining ethyl acetate solvent. The polymer was particulate and free-flowing with average particle size of less than 10 microns and had the bioadhesive property. Its Brookfield viscosity at 1% mucilage in water was 59,200 cPs measured at 20 rpm, and a pH of about 7.5.

In additional runs made using the process and percentages of the Example, that the amount of divinyl glycol crosslinker used was 2.0% by weight based upon the weight of the acrylic acid monomer (217.7 grams) and at 1.5% by weight based upon the weight of the acrylic acid monomer (163.28 grams). The recovered polymer had a Brookfield viscosity at 1% mucilage in water, 20 rpm, and a 7.5 pH, of about 22,100 to 22,300 cPs at 1.5% crosslinker level and ranged from 28,500 to 54,000 cPs at 2.0% crosslinker level. The polymers exhibited the bioadhesive property.

In summary, the process of the present invention produces a polymer which as the bioadhesive attributes of polycarbophil, has a small particle size of less than 10 microns, without grinding, and a Brookfield viscosity at 1% by weight in water of greater than about 20,000 cPs.

The foregoing embodiments of the present invention have been presented for purposes of illustration and description. These description and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated. It is intended that the invention be defined by the following claims.

I claim:

1. Process for preparing a crosslinked polyacrylic acid polymer which has a particle size of less than 10 microns without grinding and which has Brookfield viscosity of greater than about 20,000 cPs in the form of a 1% by weight thereof in water, said process comprising polymerizing acrylic acid monomer, which has up to 10% of the acrylic acid neutralized, in a solvent selected from acetone, alkyl acetates of 1 to 6 carbon atoms in the alkyl group, and mixtures thereof, wherein the solvent contains less than about 1% water, in the presence of divinyl glycol crosslinker and an initiator.

2. Process of claim 1 wherein the solvent is selected from alkyl acetates having 2 to 4 carbons in the alkyl group, and mixtures thereof, wherein amount of the initiator is 0.05 to 2%, based on the weight of the monomer; and wherein amount of the crosslinker is 0.01 to 3%, based on the weight of the monomer.

3. Process of claim 2 wherein the solvent is ethyl acetate and the crosslinked polyacrylic acid has bioadhesive property.

4. The process of claim 1 wherein the crosslinked polyacrylic acid polymer has a Brookfield viscosity of greater than about 50,000 cPs.

5. Process of claim 3 wherein the initiator is selected from di(2-ethylhexyl) peroxydicarbonate, di(sec-butyl) peroxydicarbonate, di(n-propyl) peroxydicarbonate, lauroyl peroxide, and mixtures thereof; and wherein the polyacrylic acid is not washed with water immediately after the acrylic acid monomer is polymerized.

6. Process of claim 5 wherein the monomer concentration in the ethyl acetate solvent is about 10–20% by weight, wherein amount of the crosslinker is 0.5 to 2% by weight; wherein amount of the initiator is 0.1 to 1% by weight; and wherein 1 to 5% of the carboxyl groups in the acrylic acid is neutralized.

7. Crosslinked acrylic acid polymer made by the process of claim 1, which has particle size of less than 10 microns as obtained without grinding, a viscosity of greater than about 20,000 cPs when measured in water at 1% by weight concentration, and a bioadhesive property with respect to a mucous membrane.

8. Polymer of claim 7 which has bioadhesive property of at least 50 dynes/cm² when adhesion is measured between two pieces of freshly excised rabbit stomach tissue.

9. The polymer of claim 7 wherein said viscosity is greater than about 50,000 cPs.

10. Polymer of claim 7 prepared in presence of ethyl acetate solvent.

* * * * *